United States Patent [19]

Rupp et al.

[11] 4,168,963
[45] Sep. 25, 1979

[54] HERBICIDAL AGENTS

[75] Inventors: Walter Rupp, Königstein, Taunus;
Manfred Finke, Kelkheim; Hermann
Bieringer, Eppstein, Taunus; Peter
Langelüddeke, Hofheim am Taunus;
Hans-Jerg Kleiner, Kronberg,
Taunus, all of Fed. Rep. of Germany

[73] Assignee: Hoechst Aktiengesellschaft,
Frankfurt am Main, Fed. Rep. of
Germany

[21] Appl. No.: 797,171

[22] Filed: May 16, 1977

[30] Foreign Application Priority Data

May 17, 1976 [CH] Switzerland .................. 6153/76

[51] Int. Cl.² ............................................. A01N 9/36
[52] U.S. Cl. .......................................... 71/86; 71/87
[58] Field of Search ......................... 71/86, 87

[56] References Cited
PUBLICATIONS

German Patent Specification No. 116236, Roez. Chem. 49, 2129 (1975).

Primary Examiner—Catherine L. Mills
Attorney, Agent, or Firm—Curtis, Morris & Safford

[57] ABSTRACT

Herbicidal agents, containing as active ingredient a compound of the formula

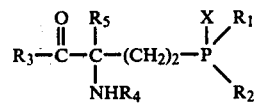

or their salts with acids, are useful for combatting a great variety of mono- and dicotyledonous weeds. In the formula $R_1$ is methyl or halomethyl, $R_2$ is OH, SH, OM or SM (M=equivalent of a base), $R_3$ is the same as $R_2$ or an ester, amide or hydrazide group, $R_4$ and $R_5$ are preferably hydrogen and X is oxygen or sulfur.

12 Claims, No Drawings

HERBICIDAL AGENTS

The subject matter of the invention is herbicidal agents, characterised by their content of compounds of the general formula $$\underset{R_4-NH}{\overset{\overset{O}{\underset{\|}{R_3-C}}\underset{|}{\overset{R_5}{\underset{|}{-C}}}-(CH_2)_2-\overset{X}{\underset{\|}{P}}\underset{R_2}{\overset{R_1}{\diagup}}}{}} \cdot (HY)_m \tag{I}$$

in which $R_1$ represents methyl, which may optionally be halogenated 1 to 3 times, preferably chlorinated, $R_2$ represents —OH, —SH, —OM or —SM (wherein M is the equivalent of an inorganic or organic base), $R_3$ represents (a) —OH, —SH, —OM or —SM, (b) ($C_1$–$C_{12}$)-alkoxy, ($C_3$–$C_8$)-cycloalkoxy, ($C_2$–$C_6$)-alkenyloxy, ($C_3$–$C_6$)-alkynyloxy, phenoxy, phenoxyphenoxy or benzyloxy as well as the corresponding thio analogs of these radicals, wherein the said groups may in turn be substituted by OH, halogen, $CF_3$, $NH_2$, $NO_2$, ($C_1$–$C_4$)-alkyl, ($C_1$–$C_4$)-alkoxy, carboxyl, ($C_1$–$C_6$)-alkoxycarbonyl, ($C_1$–$C_4$)-alkylamino, di-($C_1$–$C_4$)-alkylamino, piperidino, pyrrolidino, piperazino or morpholino.

(c) amino, ($C_1$–$C_4$)-alkylamino, di-($C_1$–$C_4$)-alkylamino, ($C_7$–$C_{10}$)-phenalkylamino, di-($C_7$–$C_{10}$)-phenalkylamino, wherein the said groups may in turn be substituted by OH, ($C_1$–$C_4$)-alkyl, ($C_1$–$C_4$)-alkylamino, di-($C_1$–$C_4$)-alkylamino, ($C_1$–$C_4$)-alkoxy, halogen or carboxyl; hydrazino, β-($C_1$–$C_4$)-alkylhydrazino, β,β-di-($C_1$–$C_4$)alkylhydrazino, ($C_1$–$C_{12}$)acyloxy, halogen-($C_1$–$C_{12}$)-acyloxy, piperidino, pyrrolidino, piperazino, morpholino or anilino, which is optionally substituted once or twice in the phenyl ring by ($C_1$–$C_4$)-alkyl, F, Cl, Br, $NO_2$, OH, $CCl_3$, $CF_3$, ($C_1$–$C_4$)-alkylamino, di-($C_1$–$C_4$)-alkylamino, ($C_1$–$C_4$)-alkoxy, phenoxy or phenylamino, $R_4$ represents hydrogen, ($C_1$–$C_4$)-acyl, halogen-($C_1$–$C_4$)-acyl, benzoyl or radicals of the formula

—C(X)NR_6R_7

$R_5$ represents hydrogen or ($C_1$–$C_4$)-alkyl, $R_6$ represents hydrogen or ($C_1$–$C_4$)-alkyl, $R_7$ represents hydrogen, ($C_1$–$C_4$)-alkyl or phenyl, which is optionally substituted in the phenyl ring, preferably substituted once or twice, by ($C_1$–$C_4$)-alkyl, F, Cl, Br, $NO_2$, $CCl_3$, $CF_3$, X represents oxygen or sulfur, Y represents the anion of an inorganic or organic acid having a dissociation constant $>10^{-3}$, m represents 0, ½ or 1.

The aliphatic groups mentioned for $R_3$ are, if substituted, preferably substituted one to three times, in particular once, by hydroxy, ($C_1$–$C_4$)-alkoxy and/or halogen, especially chlorine. The aromatic groups may be substituted one to three times, preferably once or twice, preferably by halogen, especially chlorine, by $CF_3$, ($C_1$–$C_2$)-alkoxy, nitro, amino, ($C_1$–$C_2$)-alkylamino, di-($C_1$–$C_2$)-alkylamino, carboxyl and/or carboxyalkyl having up to 3 C-atoms.

Preferred radicals are:

$R_1$: methyl, chloromethyl, especially methyl, $R_2$: OH, OM, $R_3$: OH, ($C_1$–$C_4$)-alkoxy, 2-hydroxyethoxy, 4-hydroxybutoxy, allyloxy, —$NH_2$, —NH—$NH_2$ or OM, in which M: Na, K, ½ Cu, ½ Mg, ½ Ca, ½ Zn, ½ Ni, ½ Mn, ½ Fe, $NH_4$, ($C_1$–$C_4$)-alkylammonium, di-($C_1$–$C_4$)-alkylammonium, tri-($C_1$–$C_4$)-alkylammonium or $C_6H_5NH_3$; in which where $R_2$ or $R_3$ represents OM, m=0. Particularly preferred meanings for $R_3$ are OH, $OCH_3$, ONa, OK, $ONH_4$, ($C_1$–$C_4$)alkylammonium, di-($C_1$–$C_4$)alkylammonium, tri-($C_1$–$C_4$)-alkylammonium, as well as compounds of the formula I, in which $R_2=R_3=$OM $R_4$: hydrogen, $R_5$: hydrogen or methyl, especially hydrogen.

The acids HY that come into consideration are chiefly strong mineral acids such as HCl and $H_2SO_4$. The compounds of the formula I may also form salts with other strong acids such as HBr, $H_3PO_4$, $HClO_4$, $HNO_3$ inter alia, wherein for dibasic acids, m may be ½.

X preferably represents oxygen.

Some compounds of the formula I and processes for their manufacture are known in the literature (German Patent Specification No. 116 236, Rocz. Chem. 49, 2129 (1975)), but most of the compounds are new and may be manufactured according to analogous processes (J. Org. Chem. 29, 832 (1964)).

The compounds of the formula I may be prepared, for example, by nucleophilic substitution of halogenoethylphosphinic acid esters with acetaminomalonic acid esters in the presence of molar amounts of a strong base, and subsequent saponification and decarboxylation of the resulting intermediate product (Japanese Application No. 7 391 019):

$$\underset{C_2H_5O}{\overset{CH_3}{\diagup}}\overset{O}{\underset{\|}{P}}(CH_2)_2Br + \underset{\underset{\overset{\|}{O}}{\overset{|}{NHCCH_3}}}{NaC(COOC_2H_5)_2} \xrightarrow{-NaBr}$$

$$\underset{C_2H_5O}{\overset{CH_3}{\diagup}}\overset{O}{\underset{\|}{P}}(CH_2)_2\underset{\underset{\overset{\|}{O}}{\overset{|}{NHCCH_3}}}{C(COOC_2H_5)_2} \xrightarrow{HCl}$$

$$\underset{HO}{\overset{CH_3}{\diagup}}\overset{O}{\underset{\|}{P}}(CH_2)_2\underset{NH_2}{\overset{|}{CH}}-COOH \cdot HCl$$

3-amino-3-carboxypropylphosphinic acid may also be prepared by adding acetylaminomalonic acid esters to vinylphosphinic acid esters in the presence of catalytic amounts of a strong base, and subsequent saponification of the adduct:

$$\underset{ClCH_2CH_2O}{\overset{CH_3}{\diagup}}\overset{O}{\underset{\|}{P}}CH=CH_2 + \underset{\underset{\overset{\|}{O}}{\overset{|}{NHC-CH_3}}}{HC(COOC_2H_5)_2} \xrightarrow{NaOC_2H_5}$$

-continued

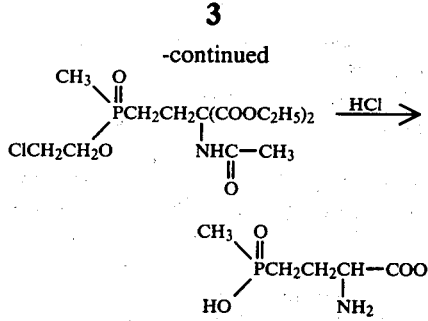

A further method considered for the preparation of the compounds of the formula I is, for example, the Streckersche synthesis:

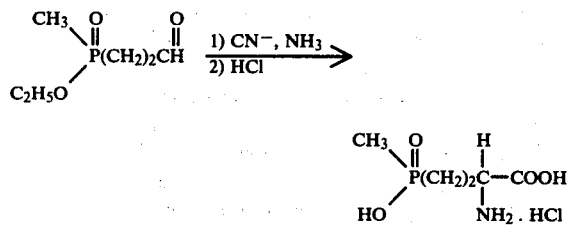

It is possible to produce from the compounds of the general formula I further derivatives of the formula I according to processes known per se, for example esterification, alkylation, acylation, salt formation or amidation.

Compounds of the formula I that come into consideration are, for example:

[(3-amino-3-carboxy)-propyl-1]-methyl-phosphinic acid and its monosodium, monopotassium, monoammonium, monolithium, diammonium, disodium, magnesium, zinc, copper, monomethylammonium, monopropylammonium, mono(diisopropylammonium), monobutylammonium, monoallylammonium, mono(diethanolammonium) salts, or the corresponding disalts; its hydrochloride, hydrobromide, hyperchlorate or hydrogen sulfate,

[(3-amino-3-carboxy)-propyl-1]-methyl-thiophosphinic acid and its monosodium, monopotassium, disodium, monomethylammonium or mono(diisopropylammonium)salts, its hydrochloride, hydrobromide, hydrogen sulfate or perchlorate;

[(3-amino-3-cyclohexyloxycarbonyl)-propyl-1]-methylphosphinic acid, its hydrochloride, sodium salt or ammonium salt;

[(3-amino-3-allyloxycarbonyl)-propyl-1]-methylphosphinic acid,

[(3-amino-3-propoxycarbonyl)-propyl-1]-methylphosphinic acid,

[(3-amino-3-(2-chloroethoxycarbonyl)-propyl-1]-methylphosphinic acid,

[(3-amino-3-carbomethoxy)-propyl-1]-methylphosphinic acid,

[(3-amino-3-carbo-n-butoxy)-propyl-1-]-methylphosphinic acid,

[(3-amino-3-carbo-n-hexyloxy)-propyl-1]-methylphosphinic acid, and their sodium, potassium, diisopropylammonium or butylammonium salts, their hydrochloride or perchlorate;

[(3-amino-3-carboethoxy)-propyl-1]-methyl-thiophosphinic acid, its sodium or propylammonium salts;

[(3-amino-3-methylaminocarbonyl)-propyl-1]-methylphosphinic acid,

[(3-amino-3-dimethylaminocarbonyl)-propyl-1]-methylphosphinic acid,

[(3-amino-3-di-n-butylaminocarbonyl)-propyl-1]-methylphosphinic acid,

[(3-amino-3-allylaminocarbonyl)-propyl-1]-methylphosphinic acid,

[(3-amino-3-propylaminocarbonyl)-propyl-1]-methylphosphinic acid,

[(3-amino-3-N-morpholinocarbonyl)-propyl-1]-methylphosphinic acid,

[(3-amino-3-N-pyrrolidinocarbonyl)-propyl-1]-methylphosphinic acid,

[(3-amino-3-N-piperidinocarbonyl)-propyl-1]-methylphosphinic acid,

[(3-amino-3-anilinocarbonyl)-propyl-1]-methylphosphinic acid,

[(3-amino-3-carbamido)-propyl-1]-methylphosphinic acid, their sodium, ammonium or diethylammonium salt or their hydrochloride,

[(3-amino-3-dibutylcarbamido)-propyl-1]-methylphosphinic acid, its sodium or butylammonium salt or its hydrochloride,

[(3-amino-3-thiocarboxy)-propyl-1]-methylphosphinic acid, its monosodium, disodium, monoammonium or diammonium salt,

[(3-amino-3-benzylaminocarbonyl)-propyl-1]-methylphosphinic acid, and its ammonium or sodium salt,

[(3-amino-3-ethylmercaptocarbonyl)-propyl-1]-methylphosphinic acid, its sodium, ammonium or diethanolammonium salt, ](3-acetylamino-3-carboxy)-propyl-1]-methylphosphinic acid, its monosodium, disodium, monoammonium or diammonium salt, or its mixed anhydride with acetic acid,

[(3-dimethylcarbamoylamino-3-carboxy)-propyl-1]-methylphosphinic acid, its monosodium, monopotassium, monoammonium, disodium, diammonium, mono(dimethylammonium) or mono(diisopropylammonium) salt,

[(3-dimethylcarbamoyl-amino-3-carbomethoxy)-propyl-1]-methylphosphinic acid, its monosodium, disodium or monobutylammonium salt,

[(3-carbamoylamino-3-carboxy)-propyl-1]-methylphosphinic acid, its monosodium, monoammonium or di-(butylammonium) salt,

[(3-carbamoylamino-3-carbomethoxy)-propyl-1]-methylphosphinic acid, or its diethylammonium salt,

[(3-thiocarbamoylamino-3-carboethoxy)-propyl-1]-methylphosphinic acid,

[(3-amino-3-methyl-3-carboxy)-propyl-1]-methylphosphinic acid, and its monosodium, disodium or monoammonium salt,

[(3-benzoylamino-3-carbophenoxy)-propyl-1]-methylphosphinic acid, and its sodium or diethanolammonium salt,

[(3-formylamino-3-carboxy)-propyl-1]-methylphosphinic acid, and its monosodium, disodium or mono(diethanolammonium) salt, and the corresponding derivatives of chloromethyl or trifluoromethyl(3-amino-3-carboxy-propyl-1)-phosphinic acid.

The compounds of the formula I exhibit a very good and very wide-ranging herbicidal action against numerous monocotyledonous and dicotyledonous weeds of many botanical families of one year and several years old. This property of action against a wide variety of weeds, which usually occur in association with each other, renders possible the use of the compounds according to the invention for combatting undesired plant growth, for example at the edges of paths, in industrial sites or railway sites, or for combatting aquatic plants. The compounds may also be used with advantage in annual and perennial agricultural crops, especially if the manner of application and/or the age of the crop plants ensures that the crop plants or their sensitive parts do not come into contact with the herbicidal substances and are thus not damaged. Examples of these are plantations, tree plantations, vine crops etc.

Since application in commercial crops before emergence does not cause or causes only slight damage to the crop plants, these compounds can be used against weeds before emergence of the seed or before sowing or after harvesting.

They may, however, also be used against plant growth, hindering harvesting, of the commercial plant itself (cotton, potatoes).

The subject matter of the invention is therefore also the use of compounds of the formula I for combatting weeds.

The agents according to the invention contain the active substances according to the general formula I in an amount of 2–95%. Since the active substances are partially water-soluble, they may advantageously be used in the form of aqueous solutions. Otherwise, it is possible to use as emulsifiable concentrates, wettable powders and sprayable solutions in the customary forms of preparation if they are not themselves water-soluble. Wettable powders are preparations uniformly dispersible in water that contain in addition to the active substance, apart from a diluent or inert substance, wetting agents, for example, polyoxethylated alkyl phenols, polyoxethylated oleyl or stearyl amines, alkyl or alkylphenyl sulphonates and dispersing agents, for example, a sodium salt of ligninsulfonic acid, a sodium salt of 2,2′-dinaphthylmethane-6,6′-disulfonic acid, a sodium salt of dibutylnaphthalenesulfonic acid or also a sodium salt of oleylmethyltaurine acid.

Emulsifiable concentrates are obtained by dissolving the active substance in an organic solvent, for example butanol, cyclohexanone, xylene or also aromatic substances of higher boiling points.

To achieve good suspensions or emulsions in water, wetting agents from the above-mentioned series are furthermore added.

Sprayable solutions, as handled widely in spray packs, contain the active substance dissolved in an organic solvent, and the propellant used is, for example, a mixture of fluorochlorohydrocarbons.

In herbicidal agents, the concentrations of the active substances in the commercially customary formulations may be different. In wettable powders the concentration of active substance varies for example, between approximately 10% and 80%, the remainder consisting of the above-mentioned formulation additives. In emulsifiable concentrates the concentration of active substance is approximately 10 to 60%.

For application, the commercially customary concentrates are, if necessary, diluted in the usual manner, for example by means of water in the case of wettable powders and emulsifiable concentrates. Sprayable solutions are not diluted with further inert substances before use. The required application quantity varies depending on the external conditions, such as temperature, moisture, inter alia. It can vary within wide limits, for example between 0.1 kg/ha and 10 kg/ha of active substance, but is preferably between 0.3 and 3 kg/ha.

EXAMPLE 1

[(3-Amino-3-carboxy)-propyl-1]-methylphosphinic acid hydrochloride 22 g (0.164 mole) of methyl-vinyl-phosphinic acid ethyl ester and 35 g (0.161 mole) of acetaminomalonic acid diethyl ester are heated together to 80° C. and after removing the heating bath, 3–5 ml of a 2% ethanolic sodium ethylate solution are added. After a few minutes the reaction temperature increases to 90°–95° C. After the exothermic reaction has died down, stirring is continued for approximately 4 hours at 80°–85° C.

500 ml of 25% hydrochloric acid is added to the oily reaction product and the whole is heated under reflux for 6 hours. After evaporating the reaction solution in vacuo 38 g (92% of the theoretical yield) of [(3-amino-3-carboxy)-propyl-1]-methylphosphinic acid hydrochloride remain. The product melts at 194°–198° C. with decomposition (Lit. mp: 195°–198° C., German Democratic Republic Specification No. 116,236).

EXAMPLE 2

[(3-Amino-3-carboxy)-propyl-1]-methylphosphinic acid 120 g (2.07 mole) of propylene oxide are added dropwise at approximately 25° C. to a solution in 1.2 l of 80% ethanol of 220 g (1.01 mole) of [(3-amino-3-carboxy)-propyl-1]-methylphosphinic acid hydrochloride. The reaction temperature is held at approximately 25°–30° C. during the dropwise addition. The reaction solution is subsequently cooled to 0° C. After approximately 3–4 hours the crystalline precipitate is suction filtered, washed with 94% ethanol and the product is dried at 100° C. in a vacuum chamber. 163 g (89% of the theoretical yield) of [(3-amino-3-carboxy)-propyl-1]-methylphosphinic acid are obtained. The amino acid melts at 229°–231° C. (Lit.: 241°–242° C., ROCZ, Chem. 49, 2129 (1975)) with decomposition.

EXAMPLE 3

Copper salt of [(3-amino-3-carboxy)-propyl-1]-methylphosphinic acid 18.1 g (0.1 mole) of [(3-amino-3-carboxy)-propyl-1]-methylphosphinic acid are dissolved in 100 ml of water at 70° C. and heated under reflux for 3 hours together with 11.5 g (0.1 mole) of $CuCO_3.Cu(OH)_2.0.5\ H_2O$. After cooling the reaction mixture the light blue salt is suction filtered. 17.5 g (72% of the theoretical yield) of copper salt of [(3-amino-3-carboxy)-propyl-1]-methylphosphinic acid, which melts at 257°–258° C. with decomposition, is obtained.

EXAMPLE 4

Disodium salt of [(3-amino-3-carboxy)-propyl-1]-methylphosphinic acid

A solution of 8 g (0.2 mole) of NaOH in 20 ml of water is added dropwise at 70° C. to a solution of 18.1 g (0.1 mole) of [(3-amino-3-carboxy)-propyl-1]-methylphosphinic acid in 100 ml of water. The solvent is distilled off under reduced pressure and the residue is dried at 80° C. under an oil pump vacuum. 21.8 g (97% of the theoretical yield) of disodium salt of [(3-amino-3-carboxy)-propyl-1]-methylphosphinic acid, which melts at 300° C. with decomposition, is obtained.

EXAMPLE 5

[(3-Amino-3-carbomethoxy)-propyl-1]-methylphosphinic acid

Hydrogen chloride is introduced into a paste of 100 g (0.46 mole) of [(3-amino-3-carboxy)-propyl-1]-methylphosphinic acid hydrochloride in 500 ml of methanol. The temperature thereby increases to 60° C. and a clear solution results. Stirring is carried out for 1 hour at 60° C., the methanol is evaporated off in vacuo, 300 ml of fresh methanol are added to the residue and hydrogen chloride is passed through the reaction solution again for 4 hours.

After evaporation, the residue is taken up in 150 ml of methanol and the solvent is distilled off again. This operation is repeated twice more. The residue is then taken up in 500 ml of methanol and propylene oxide is added until no more chloride ions can be detected in the solution. The solution is left to stand overnight at 0° C., the precipitated product is suction filtered and, by drying, 70 g (78% of the theoretical yield) of methyl ester, which does not decompose below 105° C., are obtained.

EXAMPLE 5a

[(3-Amino-3-carboethoxy)-propyl-1]-methylphosphinic acid hydrochloride

Hydrogen chloride gas is introduced into a paste of 21.75 g (0.1 mole) of [(3-amino-3-carboxy)-propyl-1]-methylphosphinic acid hydrochloride in 100 ml of ethanol. The reaction temperature thereby increases to 74° C. Stirring is carried out for 1 hour at this temperature. Subsequently the excess ethanol is drawn off, 100 ml of fresh ethanol are added to the residue and hydrogen chloride gas is passed through the reaction solution at 75° C. for 4 hours. Undissolved portions are then filtered off, the solvent is evaporated off under reduced pressure and the residue is dried in an oil pump vacuum. 21 g (85% of the theoretical yield) of ethyl ester hydrochloride are obtained. The product is glass-like and strongly hygroscopic, so that a melting point could not be determined.

EXAMPLE 6

[(3-Amino-3-carbamido)-propyl-1]-methylphosphinic acid 100 ml of a methanol solution saturated with ammonia gas are added, while cooling with ice, to 15 g (0.768) of [(3-amino-3-carbomethoxy)-propyl-1]-methylphosphinic acid in a pressure vessel. The reaction mixture is shaken at room temperature for 4 days. Subsequently, the solvent and the excess ammonia are distilled off, and the residue is dried in an oil pump vacuum. 12 g (87% of the theoretical yield) of [(3-amino-3-carbamido)-propyl-1]-methylphosphinic acid, which melts at 245° C. with decomposition, are obtained.

EXAMPLE 7

[(3-Amino-3-carbanilido)-propyl-1]-methylphosphinic acid 19.5 g (0.1 mole) of [(3-amino-3-carbomethoxy)-propyl-1]-methylphosphinic acid are mixed with 30 g (0.32 mole) of aniline and heated for 5 hours at 140° C. the methanol being distilled off. After cooling, the residue solidifies to a lacquer-like brown mass, which is extracted by boiling four times with 50 ml of benzene. The residue is made into a paste with a little water, and goes into solution. After a few minutes the anilide cyystallizes out. It is suction filtered, washed with a little water, and recrystallized from water. 9.3 g (40% of the theoretical yield) of anilide, which melts at 253°-254° C. with decomposition, are obtained.

The following compounds are obtained in a similar manner to that in Examples 1 to 7:

Table 1

$$R_3-\overset{O}{\overset{\|}{C}}-\overset{R_5}{\underset{R_4-NH}{C}}-(CH_2)_2\overset{X}{\overset{\|}{P}}\overset{R_1}{\underset{R_2}{\diagup}}$$

($R_1$ = CH$_3$, $R_4$ = $R_5$ = H, X = O)

| Example No. | R$_2$ | R$_3$ | Mp. (°C.) | Produced according to Example |
|---|---|---|---|---|
| 8 | O$^-$Na$^+$ | OH | 165–170 | 4 |
| 9 | O$^-$N$^+$H$_3$CH(CH$_3$)$_2$ | OH | 105 | 4 |
| 10 | O$^-$N$^+$H$_3$n-C$_4$H$_9$ | OH | 192–193 | 4 |
| 11 | O$^-$N$^+$H$_4$ | O$^-$N$^+$H$_4$ | (+) | 4 |
| 12 | OH | OC$_2$H$_5$ | 74 | 5 |
| 13 | OH | OC$_4$H$_9$(n) | 165–166 | 5 |
| 13a | | hydrochloride of 13 | (+) | 5a |
| 14 | OH | OCH$_2$CH$_2$OH | (+) | 5 |
| 15 | OH | OCH$_2$CH$_2$CH$_2$OH | (+) | 5 |
| 16 | OH | OCH$_2$CH$_2$CH$_2$CH$_2$OH | 147–149 | 5 |
| 17 | OH | NHNH$_2$ | 189 | 6 |

(+) strongly hygroscopic, melting point indeterminable

EXAMPLE 18

[(3-Methyl-3-amino-3-carboxy]-propyl-(1)-methylphosphinic acid 136 g (1 mole) of the mono-n-butyl ester of methanephosphonous acid are heated at 50° C. for 48 hours with 70 g (1 mole) of methylvinyl ketone in the presence of 0.1 g of hydroquinone and 2 ml of tetramethyl guanidine. In the course of the reaction a further 5 ml of tetramethyl guanidine are added dropwise. Subsequently distillation is carried out under reduced pressure. Yield: 28.5 g of 3-oxo-butylmethylphosphinic acid-n-butyl ester, bp$_{0.3}$: 130° C.

20.6 g (0.1 mole) of this intermediate product are mixed at 15° C. with 5.8 ml (0.15 mole) of HCN and 1 ml of triethylamine and the whole is left to stand for 24 hours. After removing the excess HCN, 50 ml of ethanol and 34.2 g (0.3 mole) of (NH$_4$)$_2$CO$_3$ are added and the reaction mixture is stirred for 4 hours at 50° to 55° C. and half an hour at 75° C.

The mixture is then cooled, filtered and concentrated, a viscous, dark residue remaining. This is extracted several times with boiling acetonitrile. 5.8 g of 5-methyl-5-[β-(n-butylmethanephosphonyl)-ethyl]-hydantoin crystallize out from the extracts. 5.8 g (0.021 mole) of the resulting hydantoin are heated with 100 ml of 1 N NaOH for 1.5 hours at 150° C. in an autoclave. Subsequently the mixture is acidified with HCl and evaporated to dryness.

The resulting hydrochloride of [3-methyl-3-amino-3-carboxyl]-propyl-(1)-methylphosphinic acid is separated from the inorganic salts by extracting with 99.5% alcohol. After concentrating to dryness and taking up in 70% alcohol, 2.5 g of [3-methyl-3-amino-3-carboxy]-propyl-(1)-methylphosphinic acid crystallize out after releasing the amino group with propylene oxide with one mole of water of crystallization (mp. 169° C.).

Formulation example:

A wettable powder readily dispersible in water is obtained by mixing and grinding in a pin mill:

| | |
|---|---|
| 25 parts by weight | of active substance |
| 64 parts by weight | of kaolin-contaning quartz as inert substance |
| 10 parts by weight | of a potassium salt of ligninsulfonic acid, and |
| 1 part by weight | of a sodium salt of oleyl-methyltaurine acid as wetting and dispersing agent. |

BIOLOGICAL EXAMPLES

EXAMPLE I: (Post-emergence application)

Seeds of a very wide variety of weeds from numerous botanical groups are sown in pots and grown under appropriate greenhouse conditions for 3–5 weeks to a size of 3–12 cm depending on the type of plant. Subsequently, the compound from Example (1) in the form of a spray powder is sprayed in various dosages onto the plants. After standing for 14 days in the greenhouse, the action of the preparations is evaluated visually.

Apart from the plants grown from seed, 3 grass-type weeds several years old are included in the tests, these being damaging weeds that are economically extremely important throughout the world, namely couch grass (Agropyron), Bermuda grass (Cynodon) and *Cyperus rotundus*. Rhizome pieces of these plants are transplanted into pots and grown in the greenhouse for 5–6 weeks until the plants have reached a size of 12–15 cm. They are then sprayed with the compounds according to the invention. The evaluation of the results is carried out after 14 days.

The results of the tests are compiled in Table 2, the evaluation having been under taken according to Bolle's scheme (Nachrichtenblatt des Deutschen Pflanzenschutzdienstes 16, 1964, 92–94) (see evaluation scheme). The test results show that the compound according to the invention successfully combats important, economically significant types of weed, especially such important weeds as Ipomoea and other dicotyledons, as well as weeds several years old such as *Cyperus rotundus*.

| | Evaluation Scheme: | |
|---|---|---|
| Evaluation | Damaging action in % on | |
| number | Weeds | Crops |
| 1 | 100 | 0 |
| 2 | 97.5 to <100 | >0 to 2.5 |
| 3 | 95 to <97.5 | >2.5 to 5 |
| 4 | 90 to <95 | >5 to 10 |
| 5 | 85 to <90 | >10 to 15 |
| 6 | 75 to <85 | >15 to 25 |
| 7 | 65 to <75 | >25 to 35 |
| 8 | 32.5 to <65 | >35 to 67.5 |
| 9 | 0 to <32.5 | >67.5 to 100 |

Table 2

| Compound (Example) | Dose (kg/ha A.S.) | Biological action in post-emergence method — Type of Plant | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| 2 | 2.5 | 1 | 1 | 1 | 1 | 1 | 1 | 1 | 4 | 1 | 1 | 1 | 1 |
| | 0.6 | 2 | 2 | 1 | 2 | 1 | 2 | 6 | 4 | 1 | 3 | 1 | 1 |
| 9 | 2.5 | 1 | 2 | 2 | 1 | 1 | 2 | 1 | 1 | 1 | 1 | 1 | 1 |
| | 0.6 | 2 | 5 | 2 | 3 | 2 | 2 | 4 | 4 | 4 | 3 | 1 | 4 |
| 4 | 2.5 | 1 | 4 | 1 | 2 | 1 | 1 | 1 | 2 | 1 | 1 | 1 | 1 |
| | 0.6 | 2 | 3 | 2 | 4 | 1 | 2 | 4 | 4 | 1 | 6 | 2 | 5 |
| 8 | 2.5 | 1 | 3 | 1 | 1 | 1 | 1 | 1 | 2 | 1 | 1 | 1 | 2 |
| | 0.6 | 4 | 5 | 2 | 3 | 1 | 1 | 3 | 1 | 2 | 1 | 1 | 3 |
| 10 | 2.5 | 1 | 1 | 2 | 1 | 1 | 2 | 1 | 3 | 1 | 1 | 1 | 2 |
| | 0.6 | 1 | 4 | 2 | 3 | 1 | 4 | 1 | 4 | 1 | 2 | 1 | 5 |
| 3 | 2.5 | 1 | 1 | 1 | 5 | 5 | 4 | 6 | 6 | 1 | 6 | — | 6 |
| | 0.6 | 1 | 1 | 2 | 7 | 5 | 7 | 8 | 8 | 4 | 8 | — | 7 |
| 5 | 2.5 | 1 | 1 | 1 | 1 | 1 | 3 | 4 | 3 | 1 | 1 | 2 | 1 |
| | 0.6 | 1 | 1 | 1 | 2 | 1 | 6 | 7 | 7 | 4 | 7 | 7 | 7 |
| 11 | 2.5 | 1 | 1 | 1 | 1 | 1 | 1 | 1 | 1 | 1 | 1 | 1 | 1 |
| | 0.6 | 1 | 3 | 1 | 1 | 1 | 5 | 6 | 6 | 1 | 3 | 4 | 5 |
| 12 | 2.5 | 1 | 1 | 1 | 2 | 1 | 4 | 3 | 1 | 1 | 2 | 4 | 1 |
| | 0.6 | 1 | 5 | 1 | 1 | 1 | 7 | 7 | 8 | 4 | 7 | 7 | 7 |
| 13 | 2.5 | 1 | 1 | 1 | 1 | 1 | 4 | 6 | 5 | 1 | 1 | 4 | 2 |
| | 0.6 | 1 | 1 | 2 | 1 | 1 | 5 | 8 | 8 | 2 | 8 | 8 | 4 |
| 17 | 2.5 | 1 | 1 | 1 | 1 | 1 | 4 | 7 | 5 | 1 | 1 | 8 | 2 |
| | 0.6 | 2 | 1 | 5 | 1 | 2 | 8 | 8 | — | 1 | 8 | — | 7 |
| 6 | 2.5 | 1 | 1 | 1 | 1 | 1 | 1 | 7 | 4 | 1 | 1 | 1 | 1 |
| | 0.6 | 1 | 1 | 1 | 1 | 1 | 6 | 8 | 8 | 2 | 8 | 7 | 5 |
| 16 | 2.5 | 1 | 1 | 1 | 1 | 1 | 3 | 7 | 6 | 1 | 1 | 2 | 1 |
| | 0.6 | 1 | 1 | 2 | 1 | 1 | 6 | 8 | 8 | 1 | 7 | 7 | 6 |
| 14 | 2.5 | 1 | 1 | 1 | 1 | 1 | 3 | 6 | 7 | 1 | 1 | 5 | 1 |
| | 0.6 | 1 | 1 | 2 | 1 | 1 | 7 | 8 | — | 2 | 7 | 8 | 1 |
| 15 | 2.5 | 1 | 1 | 1 | 1 | 1 | 5 | 7 | 8 | 1 | 3 | 6 | 1 |
| | 0.6 | 2 | 3 | 6 | 1 | 1 | 8 | — | — | — | — | — | — |
| 1 | 2.5 | 1 | 1 | 1 | 1 | 1 | 1 | 1 | 1 | 1 | 2 | 2 | 2 |

Table 2-continued

| Compound (Example) | Dose (kg/ha A.S.) | Type of Plant | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| 7 | 0.6 | 1 | 1 | 2 | 3 | 1 | 1 | 6 | 4 | 1 | 3 | 3 | 3 |
| | 4.0 | 1 | — | — | 1 | — | — | — | — | — | — | — | — |
| 18 | 2.5 | 3 | 4 | 6 | 5 | 1 | 5 | 7 | — | 5 | — | — | 3 |
| | 0.6 | 3 | 5 | 7 | 6 | 1 | 6 | 8 | — | 7 | — | — | 4 |

Key:
Type of plant
1 = Sinapis
2 = Matricaria
3 = Chrysanthemum
4 = Stellaria
5 = Amaranthus
6 = Ipomoea
7 = Avena
8 = Alopecurus
9 = Setaria
10 = Poa
11 = Lolium
12 = Echinochloa
A.S. = active substance

What is claimed is:

1. A method for combating undesired plant growth which comprises applying to the infected areas an herbicidally effective quantity of an herbicidal agent having as an essential active ingredient a compound of the formula:

$$R_3-\overset{O}{\overset{\|}{C}}-\overset{R_5}{\underset{\underset{R_4}{\overset{|}{NH}}}{\overset{|}{C}}}-(CH_2)_2-\overset{X}{\overset{\|}{P}}\overset{R_1}{\underset{R_2}{\diagdown}}$$

wherein
$R_1$ represents methyl,
$R_2$ represents —OH, —ONa, —ONH$_3$CH(CH$_3$)$_2$, —ONH$_3$ n-C$_4$H$_9$ or —ONH$_4$
$R_3$ represents —OH, —O—(C$_1$–C$_4$)-alkyl, amino, phenylamino, —ONH$_4$, —O(CH$_2$)$_n$OH wherein n is 2 to 4 or —NH.NH$_2$,
$R_4$ represents hydrogen,
$R_5$ represents hydrogen or methyl,
X represents oxygen, or an herbicidally effective salt of such a compound.

2. A method according to claim 1 wherein the active ingredient of the herbicidal agent is [(3-amino-3-carboxy)-propyl-1]-methylphosphinic acid.

3. A method according to claim 1 wherein the active ingredient of the herbicidal agent is [(3-amino-3-carboxy)-propyl-1]-methylphosphinic acid hydrochloride.

4. A method according to claim 1 wherein the active ingredient of the herbicidal agent is the disodium salt of [(3-amino-3-carboxy)-propyl-1]-methylphosphinic acid.

5. A method according to claim 1 wherein the active ingredient of the herbicidal agent is the monosodium salt of [(3-amino-3-carboxy)-propyl-1]-methylphosphinic acid.

6. A method according to claim 1 wherein the active ingredient of the herbicidal agent is the mono-(isopropylammonium) salt of [(3-amino-3-carboxy)-propyl-1]-methylphosphinic acid.

7. A method according to claim 1 wherein the active ingredient of the herbicidal agent is the mono(n-butylammonium)salt of [(3-amino-3-carboxy)-propyl-1]-methylphosphinic acid.

8. A method according to claim 1 wherein the active ingredient of the herbicidal agent is the diammonium salt of [(3-amino-3-carboxy)-propyl-1]-methylphosphinic acid.

9. A method according to claim 1 wherein the active ingredient of the herbicidal agent is the monoammonium salt of [(3-amino-3-carboxy)-propyl-1]-methylphosphinic acid.

10. A method according to claim 1 wherein the active ingredient of the herbicidal agent is [(3-amino-3-carbamido)-propyl-1]-methylphosphinic acid.

11. A method according to claim 1 wherein the active ingredient of the herbicidal agent is the monopotassium salt of [(3-amino-3-carboxy)-propyl-1]-methylphosphinic acid.

12. A method according to claim 1 wherein the active ingredient of the herbicidal agent is the dipotassium salt of [(3-amino-3-carboxy)-propyl-1]-methylphosphinic acid.

* * * * *